United States Patent [19]

Summer

[11] Patent Number: 5,066,226

[45] Date of Patent: Nov. 19, 1991

[54] ORAL ORTHOPEDIC APPLIANCE FOR CORRECTING MANDIBULAR RETRUSION

[76] Inventor: John D. Summer, 427 NW. 23rd St., Portland, Oreg. 97210-2615

[21] Appl. No.: 613,112

[22] Filed: Nov. 13, 1990

Related U.S. Application Data

[63] Continuation-in-part of Ser. No. 263,087, Oct. 27, 1988, Pat. No. 4,969,822.

[51] Int. Cl.$^5$ ............................................. A61C 3/00
[52] U.S. Cl. ........................................ 433/19; 433/22
[58] Field of Search .................... 433/19, 18, 21, 22, 433/12, 13, 5

[56] References Cited

U.S. PATENT DOCUMENTS

| | | | |
|---|---|---|---|
| 1,140,759 | 5/1915 | Montag | 433/12 |
| 3,618,214 | 11/1971 | Armstrong | |
| 3,798,773 | 3/1974 | Northcutt | 433/19 |
| 4,382,782 | 5/1983 | Klein et al. | 433/18 |
| 4,382,783 | 5/1983 | Rosenberg | 433/19 |
| 4,416,627 | 11/1983 | Beazley | 433/18 |
| 4,424,032 | 1/1984 | Howe | 433/19 |
| 4,462,800 | 7/1984 | Jones | 433/19 |
| 4,472,138 | 9/1984 | Howe | 433/19 |
| 4,551,095 | 11/1985 | Mason | 433/19 |
| 4,618,324 | 10/1986 | Nord | 433/19 |
| 4,795,342 | 1/1989 | Jones | 433/19 |

FOREIGN PATENT DOCUMENTS

| | | |
|---|---|---|
| 374163 | 7/1921 | Fed. Rep. of Germany . |
| 1079955 | 12/1954 | France . |

*Primary Examiner*—Cary E. O'Connor
*Attorney, Agent, or Firm*—Klarquist, Sparkman, Campbell, Leigh & Whinston

[57] ABSTRACT

A telescopic oral orthopedic appliance aligns the upper and lower jaws for treatment of the temporomandibular joint. It includes an extensible-contractable positioning device which extends between and alters the position of the mandible relative to the maxillae. The device is attached to upper and lower sets of teeth by an anchor which is embedded in a pair of opposing channel members which fit over the apex and inwardly and outwardly facing walls of the clinical crowns of a series of adjacent teeth. The length of the device is selectively variable to alter the position of the mandible forward or backward without sudden jumps or the need for removing the appliance from the mouth. The positioning device includes a rod and sleeve assembly with the rod and sleeve being restrained against relative rotation.

6 Claims, 2 Drawing Sheets

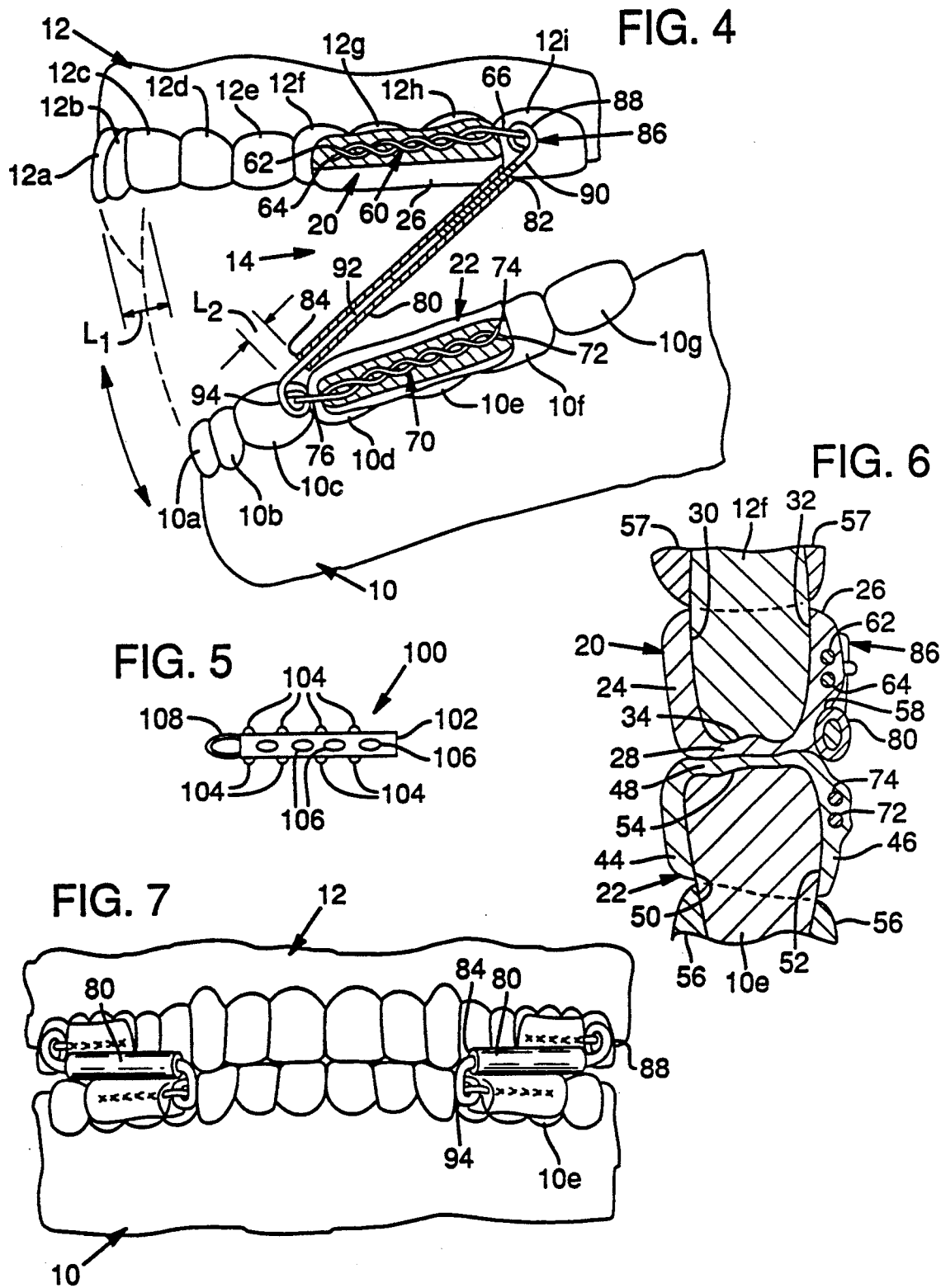

ORAL ORTHOPEDIC APPLIANCE FOR CORRECTING MANDIBULAR RETRUSION

RELATED APPLICATIONS

This application is a continuation-in-part of my prior co-pending application Ser. No. 263,087 filed Oct. 27, 1988, entitled "Oral Orthopedic Appliance for Correcting Mandibular Retrusion", now U.S. Pat. No. 4,969,822.

BACKGROUND OF THE INVENTION

1. Field of the Invention

The present invention relates to an intraoral orthopedic appliance to align the mandible and maxilla for treatment of temporomandibular joint disorders.

2. General Discussion of the Background

Mandibular retrognathia is a common cause of temporomandibular joint disorders. In this condition, a misalignment of the mandible and maxilla forces the mandible backwards into the temporomandibular joint and causes a mechanical strain which can result in dislocation of the joint or degeneration of the muscles protecting the joint. Other symptoms include tenderness in the muscles or mastication, jaw opening limitation, clicking or popping sounds in the joint, disruption of the head posture mechanism, and aggravation of middle and inner ear conditions including dizziness, tinnitus, and eustachian tube blockage.

Orthodontists have long sought a device for realigning the mandible and maxilla. An early such device was the Herbst appliance, which is shown in German Patent No. 374,163. A metal band of the Herbst appliance was placed around an upper molar and a lower incisor tooth. These two bands were interconnected by a telescopic member to exert an anteriorly directed force on the lower jar, which eventually brought the lower jaw into alignment with the upper jaw. The Herbst appliance, however, inhibited lateral movement of the jaw and it needed great strength to resist breakage from lateral jaw forces, therefore it was bulky and interfered with speaking, eating and other oral activities.

Similar telescopic devices include those shown in U.S. Pat. Nos. 3,618,214; 4,472,138; and 4,462,800, as Well as French Patent No. 1,079,955. None of these dental appliances permitted lateral jaw movement, and they all required wires or braces to attach the device to a patient's teeth. Moreover, none of these devices were suitable for treating internally deranged temporomandibular joints in which the precise position of the mandible must be easily adjustable and must, in many cases, be able to be very gradually retruded from an extremely protruded position. Such gradual return to a more normal and comfortable jaw position is important, because any sudden retrusive shift can cause redisplacement of a recaptured displaced disc.

U.S. Pat. No. 4,382,783 did disclose a telescopic, intraoral orthodontic device which could be lengthened in very fine increments to realign the mandible and maxilla. This device, however, did not permit lateral jaw action and required placement of braces or bands on the teeth for attachment.

More recently, U.S. Pat. No. 4,618,324 disclosed a telescopic orthodontic device which was attached to upper and lower molars by a pair of opposing circular bands. The telescopic portion of the device was offset laterally from the teeth and toward the inner buccal surface to avoid interference with tooth movements. Pivotal connections between the bands and telescopic device also allowed transverse movement of the jaws without damaging the orthodontic appliance. In spite of these advantages, the appliance still placed excessive strain on the individual teeth to which it was attached, leading to tooth damage or fracture. Moreover, the lateral displacement of the device from the dental arches rubbed the inner buccal surfaces and was uncomfortable.

It is accordingly an object of the present invention to provide an improved intraoral orthopedic device for aligning the mandible and maxilla.

SUMMARY OF THE INVENTION

In accordance with the present invention, a telescopic, intraoral orthopedic appliance includes an extensible-contractible positioning member that extends between and alters the position of the mandible and maxilla relative to each other. The device is attached to the upper and lower dental arches, for example by upper and lower channel-shaped attachment members which fit contiguously against a row of teeth in the maxilla and a row of teeth in the mandible. An anchor may be embedded within each attachment member and may protrude outwardly from it to present fasteners such as loops or other mechanisms to which opposite ends of the positioning device are attached. The positioning means may include a pair of hooks, or other fasteners, one at each of its opposing ends, to engage the loops of the attachment member.

The contracted or shortest length of the positioning member can be varied along the longitudinal axis of the appliance to adjust the length of the device. This adjustability feature allows gradual repositioning of the mandible without risking displacement of the articular disc, which is often caused by sudden jumps in the position of the mandible. In accordance with one specific approach, the positioning device may include a mechanism for adjusting the position of one of the fasteners to thereby adjust the length of the appliance.

In accordance with the present invention, the positioning member may comprise a telescopingly interfitting rod or shaft and a sleeve. A mechanism is provided for preventing the relative pivoting or rotation of the shaft and sleeve about the longitudinal axis of the positioning member. In the illustrated preferred embodiment, the rod and sleeve interfit or mate with one another so as to preclude relative pivoting movement. For example, the exterior surface of the rod may be oval or of some other shape so as to engage the interior surface of the sleeve, which may also be oval or of some other interfitting shape to prevent the relative pivoting movement of these components. As a result, relative rotation or pivoting movement of the rod and sleeve, which may cause a misadjustment of the length of the positioning member in some designs, is substantially eliminated.

A better understanding of the invention can be had by reference to the following drawings and detailed description.

BRIEF DESCRIPTION OF THE DRAWINGS

FIG. 4 is a view of the appliance in FIG. 1, the mouth of the user having been opened to illustrate a malocclusion being corrected by the appliance.

FIG. 5 illustrates an alternative embodiment of an anchor in accordance with the present invention.

FIG. 6 is a cross-sectional view similar to FIG. 2 illustrating an alternative configuration of a shaft and sleeve assembly of the invention.

FIG. 7 is a front elevational view, similar to FIG. 3, of the embodiment of FIG. 6 of the invention shown in position.

DETAILED DESCRIPTION OF A PREFERRED EMBODIMENT

Figure 1:
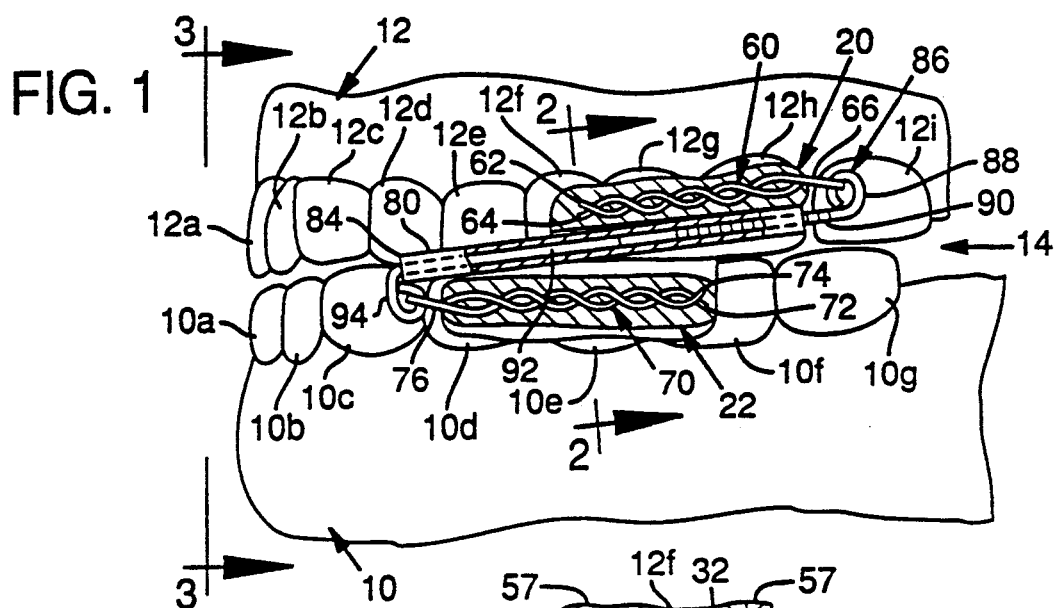
FIG. 1 is a side elevational view of the appliance of the present invention in position on a user's teeth, portions of the appliance being broken away to reveal an anchor embedded in the appliance.
Figure 3:
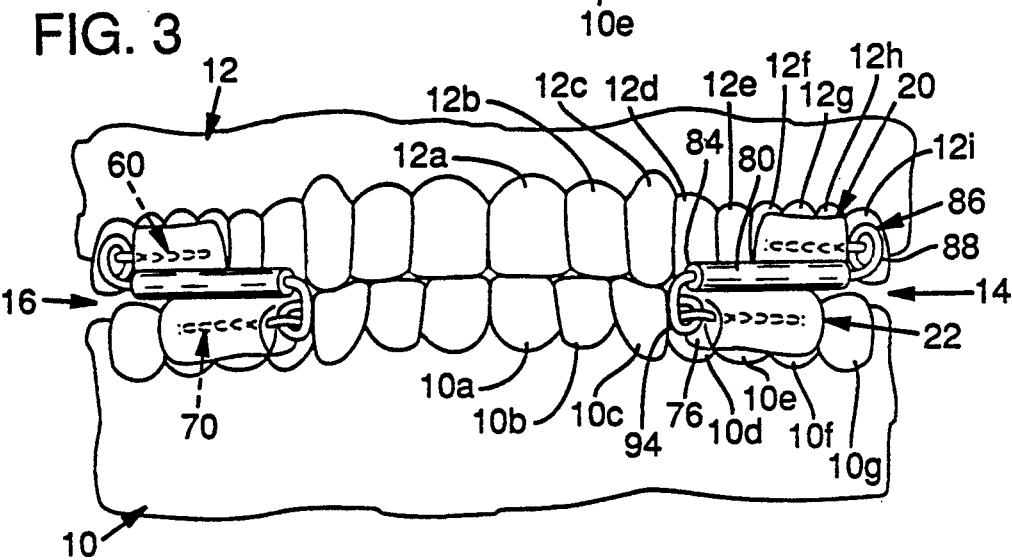
FIG. 3 is a front elevational view taken along lines 3—3 of FIG. 1.

The present invention is an orthopedic appliance for protruding the mandible. FIG. 4 illustrates retrusion of mandible 10 and the mandibular dental arch relative to maxilla 12 and the maxillary dental arch. Retrusion of the mandible 10 causes lower front tooth 10a to be set back from upper front tooth 12a by a distance L1, creating an overjet. As shown in FIG. 3, appliances 14, 16 (see also FIG. 1 for appliance 14) of the present invention protrude mandible 10 such that teeth 10a, 12a are aligned when the mouth is closed. Remaining lower teeth 10b, 10c, 10d, 10e, 10f, 10g are also brought into their proper relationship with upper teeth 12b, 12c, 12d, 12e, 12f, 12g, 12h and 12i, respectively.

Appliances 14, 16 are mirror images of one another. Hence, only appliance 14 will be described in detail.

Appliance 14 includes an upper channel member 20 and a lower channel member 22. The upper channel member has a substantially U-shaped cross section (FIG. 2) which is bounded by an inner wall 24, outer wall 26 and transverse wall 28 which fit respectively contiguously against and fit tightly around the inner surface 30, outer surface 32 and apex 34 of the clinical crowns 36 of a series of adjacent teeth 12f, 12g and 12h. Similarly, lower channel member 22 has an inner wall 44, outer wall 46 and transverse wall 48 which respectively fit contiguously against and fit tightly around the inner surface 50, outer surface 52 and apex 54 of the clinical crowns 55 of a plurality of adjacent teeth 10d, 10e and 10f. The upper and lower channel members are preferably removable, but also can be fastened in place, as by cement, if desired. Each lower tooth 10 projects from an annular alveolar bone 56 which surrounds each lower tooth, while each upper tooth 12 projects from an annular alveolar bone 57 which surrounds each upper tooth. The clinical crown 36 of each upper tooth 12 is that portion of each upper tooth 12 which is covered by enamel and projects beyond alveolar bone 57. The lower clinical crown 55 of each lower tooth 10 is that portion of each lower tooth 10 which is covered by enamel and projects beyond alveolar bone 56.

The outer wall 26 of upper channel member 20 has a recessed lower portion 58 which is recessed from the exterior surface of wall 26 approximately a distance d (FIG. 2), which is the same distance as the diameter of a sleeve 80 of the extensible-contractible member described later. Recessed portion 58 presents an arcuate outer surface which extends between transverse wall 28 and outer wall 26, and is complementary in shape to a portion of the cylindrical sleeve 80 which fits in the recess along upper channel member 20.

The outer wall 46 of lower channel member 22 has a recessed upper portion 59 which is recessed from the exterior surface of wall 46 approximately a distance d, which is the same distance as the diameter of sleeve 80. Recessed portion 59 presents an arcuate outer surface which extends between transverse wall 48 and outer wall 46, and is complementary in shape to a portion of the cylindrical sleeve 80 which fits in the recess along the lower channel member 22.

Figure 2:
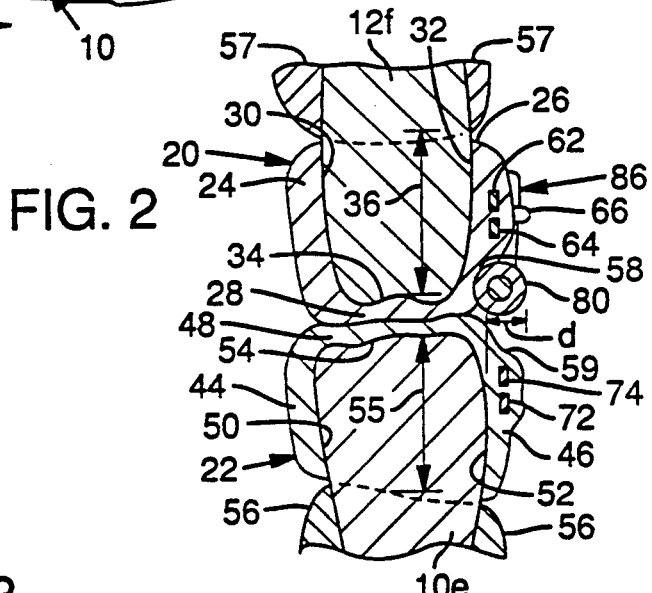
FIG. 2 is a cross sectional view taken along lines 2—2 of FIG. 1

An upper anchor 60 is embedded within outer wall 26 of upper channel member 20, and includes a pair of intertwined wires 62, 64 which are flattened into a generally vertical plane (FIG. 2) to occupy less space and minimize outward projection away from the teeth. Wires 62, 64 are embedded in wall 26. Preferably the upper channel member 20 comprises an attachment means formed of a liquid, such as acrylic, which hardens to embed the wires in place. Wires 62, 64 can thus be embedded by molding acrylic channel member 20 around the wires. The intertwined wires may be loosely helically twisted to provide small open loops through which the acrylic flows and sets to retain anchor 60 in the acrylic member 20. Wires 62, 64 are joined at a loop 66 which extends beyond a rear edge of wall 26. For strength and to prevent bending of the neck of the wires at the base of loop 66, the base of the loop is preferably embedded in the acrylic member 20. As best seen in FIG. 2, the loop 66 extends horizontally and posteriorly to upper channel member 20 above recessed portion 58. In the disclosed embodiment, only a small portion of loop 66 extends beyond the outer surface of wall 26. Other fasteners besides loops may also be used.

A lower anchor 70 is embedded within outer wall 46 of lower channel member 22, and includes a pair of helically intertwined wires 72, 74 which are flattened into a generally vertical plane to occupy less space. Wires 72, 74 are also embedded in wall 46 such as by molding acrylic around the wires such that the acrylic flows through the loops formed by the intertwined wires to securely retain the anchor 70 when the acrylic sets. Wires 72, 74 are joined at a loop 76 that extends beyond the front edge of wall 46. Like loop 66, the base of loop 76 is preferably embedded in channel member 22. Loop 76 extends horizontally anteriorly of the front edge of channel member 22 adjacent outer wall 46. A small portion of loop 76 extends beyond the outer surface of wall 46. Other fasteners besides loops may also be used.

An extensible-contractible positioning means extends between upper and lower channels 20, 22 to exert a protrusive force on mandible 10. This telescopic device includes a cylindrical tube or sleeve 80 of diameter d having a first internally threaded open end 82 and an open second end 84. A fastener, such as a first hook 86 extends from end 82 and includes a hook portion 88 which hooks into and is closed around first loop 66, and an externally threaded shaft 90 which mates with the threads inside first end 82 of sleeve 80. The threads of shaft 90 may be at a slightly different pitch than the threads of sleeve 80 and the sleeve is slightly crimped. Consequently, the shaft 90 resists turning so that no lock nut is needed. Any such locking devices could irritate a patient's cheek. Other biasing or resistance mechanisms can also, of course, be used to counter unintentional adjustment of the shaft and sleeve during use by a patient. For example, either component may be bent slightly.

An alternative mechanism may also be provided to prevent the inadvertent adjustment of the length of the positioning device, which could result if the sleeve 80 and rod 92 were to pivot or rotate relative to one another about the longitudinal axis of the positioning member assembly. Preferably this mechanism is internal to the rod and sleeve assembly so as to not irritate the patient's cheek. This mechanism may take any convenient form, but typically involves configuring the rod and sleeve to prevent their relative pivoting. Thus, for example, the exterior surface of the rod may be shaped to engage the interior surface of the sleeve while still permitting telescoping movement of these components. As a specific example, the rod or sleeve may be cooperatively shaped, such as being provided with mating projections and grooves with the projections in one element mating into longitudinal grooves on the other element. Alternatively, the rod may be shaped to have an exterior surface which engages the interior surface of the sleeve to prevent relative pivoting movement, such as having respective transverse cross-sections such that relative pivoting and rotation is prevented.

In FIGS. 6 and 7, for purposes of illustration, the rod and sleeve each are shown to have an oval cross-section such that they do not pivot or rotate relative to one another about the longitudinal axis of the positioning member and therefore can not turn and inadvertently misadjust the threaded adjustment shaft 90. A convenient manufacturing approach is simply to partially flatten both a sleeve and rod of circular cross-section to achieve the configuration shown in these figures.

The first hook 86 is substantially coplanar with a plane extending longitudinally through sleeve 80 and wall 26, and is preferably in a vertical plane as shown in the drawings. A rod 92 projects through open end 84 into sleeve 80 and reciprocates telescopically within the sleeve. Rod 92 includes a second hook 94 which hooks into and is closed around lower loop 76. Second hook 94 is preferably coplanar with a plane extending longitudinally through rod 92 and wall 46, the plane preferably being vertical as shown in the drawings.

As seen best in FIG. 2, the illustrated embodiment of appliance 16 does not extend laterally away from channel members 20, 22, but instead fits against their outer surfaces to diminish interference with oral activities and reduce damage to the mucosa of the inner buccal surface. The recesses 58, 59 cooperatively provide an indentation in walls 26, 46 in which appliance 16 fits when the mouth is closed, as shown n FIG. 2. Even when the mouth is open, as shown in FIG. 4, the appliance remains in substantially the same plane coincident with walls 26, 46. Some movement out of this plane is desirable, however, to permit lateral movement of the jaw and prevent damage to the appliance. Such lateral movement is allowed by the pivotal connections between loop 66 and hook 88 of the upper channel member, and loop 76 and hook 94 of the lower channel member.

FIG. 4 illustrates the relative position of the appliance when the mouth is fully open. A portion of rod 92 of length L2 projects out of open end 84 of sleeve 80. The distance L2 is measured from the beginning of the bent portion of hook 94 to the open end 84 of sleeve 80, and is approximately the same as the distance L1 of the overbite being corrected. As the mouth closes, rod 92 slides into sleeve 80 until hook 94 abuts end 84 to halt the inward movement of rod 92 and exert a protruding force on mandible 10 to hold it forward a distance L2 while the mouth remains closed.

Mandible 10 can be progressively protruded or allowed to retrude in small increments by slightly rotating sleeve 80 in a direction that moves threaded shaft 90 in or out of sleeve 80. As sleeve 80 rotates, the internal threads of sleeve 80 and external threads on shaft 90 force shaft 90 in or out of sleeve 80 to shorten or lengthen appliances 14, 16 and alter the protrusive force on mandible 10. This simple adjustment in the length of appliance 16 can be performed during an office visit by a dentist or by a patient at home.

Appliances 14, 16 are simple to manufacture in a laboratory or dentist's office, and are easy to install. Also, the appliance is designed so that it may be easily attached to partial or full dentures which are already being worn by the patient to replace missing teeth.

An alternate embodiment of the anchor 6 is shown in FIG. 5. This anchor 100 includes a flattened metal bar or cylinder 102 with an outer surface which is made irregular by a plurality of protuberances 104 which project outwardly from bar 102. A series of cylindrical holes 106 extend through the body of bar 102 to provide passageways through which acrylic or other moldable material flows to attach the bar to a channel member adjacent anchor 100. A loop 108 is either welded to or molded integral with bar 102 for extending out of the channel member and attaching to hooks 86, 94 of the telescopic appliance.

Having illustrated and described the principles of my invention with reference to one preferred embodiment, it should be apparent to those persons skilled in the art that such invention may be modified in arrangement and detail without departing from such principles. I claim as my invention all such modifications as come within the true spirit and scope of the following claims.

I claim:

1. A telescopic, intraoral appliance for aligning the mandible and maxilla, comprising:
    an upper attachment for attaching said appliance to said mandible and a lower attachment for attaching said appliance to said maxilla;
    a sleeve having a first end and an open second end;
    a first fastener coupled to the first end of the sleeve and coupled to one of said upper and lower attachments;
    a rod attached at one end to the other of said upper and lower attachments and having its other end projecting through said open end for reciprocating telescopic movement within said sleeve; and
    rod engagement means for restricting rotational movement of said rod relative to said sleeve.

2. The appliance of claim 1 wherein the rod and sleeve each have an oval transverse cross-section.

3. A telescopic, intraoral orthopedic appliance for aligning the mandible and maxilla, comprising:.
    an upper attachment for attaching said appliance to said mandible and a lower attachment for attaching said appliance to said maxilla;
    a sleeve having a first end and an open second end;
    a first fastener coupled to the first end of the sleeve and coupled to one of said upper and lower attachments;
    a rod attached at one end to the other of said upper and lower attachments and having its other end projecting through said open end for reciprocating telescopic movement within said sleeve; and
    the rod and sleeve being cooperatively shaped to prevent relative pivoting of the rod and sleeve.

4. A telescopic, intraoral orthopedic appliance for aligning the mandible, and maxilla, comprising:
- upper and lower channel members each having a substantially U-shaped cross section and including inner, outer and transverse walls for respectively fitting continuously against the inner surface., outer surface and apex of the clinical crowns of a plurality of adjacent teeth;
- an upper anchor means imbedded within said upper channel and a lower anchor means imbedded with said lower channel, said upper anchor means including a first fastener projecting outwardly therefrom, said lower anchor means including a second fastener projecting outwardly therefrom;
- a sleeve having a first internally threaded open end and an open second end;
- a sleeve fastener coupled to one of said first and second fasteners;
- the sleeve fastener including an externally threaded shaft portion which mates with said internally threaded first end of said sleeve; and
- a rod projecting through said open second end of the sleeve for reciprocating telescopic movement within said sleeve, said rod having a rod fastener coupled to the one of the first and second fasteners which is not coupled to the sleeve fastener and;
- said rod and said sleeve being cooperatively shaped for restricting pivoting movement of the rod relative to the sleeve while permitting reciprocating telescopic movement of the rod within said sleeve.

5. The appliance of claim 4 wherein the first and second fasteners each comprise a loop, the sleeve fastener comprises a hook and the rod fasteners comprises a hook.

6. The appliance of claim 5 wherein the rod fastener and sleeve fastener are each planar and are coplanar with a plane extending longitudinally through said rod.

* * * * *